(12) United States Patent
Liang et al.

(10) Patent No.: US 11,596,706 B2
(45) Date of Patent: Mar. 7, 2023

(54) ULTRAVIOLET AIR STERILIZER FOR DISINFECTING BACTERIUM AND VIRUS

(71) Applicant: MICROCOOL ENTERPRISE INC, Cerritos, CA (US)

(72) Inventors: Zhigang Liang, Changsha (CN); Bing Li, Changsha (CN)

(73) Assignee: MICROCOOL ENTERPRISE INC, Cerritos, CA (US)

( * ) Notice: Subject to any disclaimer, the term of this patent is extended or adjusted under 35 U.S.C. 154(b) by 358 days.

(21) Appl. No.: 16/885,354

(22) Filed: May 28, 2020

(65) Prior Publication Data

US 2021/0283296 A1   Sep. 16, 2021

(30) Foreign Application Priority Data

Mar. 12, 2020   (CN) .......................... 202020301887.9

(51) Int. Cl.
*A61L 9/20*        (2006.01)
*B01D 53/00*    (2006.01)
(Continued)

(52) U.S. Cl.
CPC ............ *A61L 9/205* (2013.01); *B01D 53/007* (2013.01); *B01D 53/0407* (2013.01); *B01D 53/0454* (2013.01); *B01D 53/346* (2013.01); *B01D 53/885* (2013.01); *H05K 7/20409* (2013.01); *A61L 2209/12* (2013.01); *A61L 2209/14* (2013.01); *B01D 2253/102* (2013.01); *B01D 2255/20707* (2013.01); *B01D 2255/802* (2013.01); *B01D 2257/90* (2013.01); *B01D 2257/91* (2013.01); *B01D 2259/804* (2013.01)

(58) Field of Classification Search
None
See application file for complete search history.

(56) References Cited

FOREIGN PATENT DOCUMENTS

CN    109395515 A   *   3/2019   ............ B01D 50/00
JP    4448558 B2   *   4/2010
(Continued)

OTHER PUBLICATIONS

He, L. CN109395515A—translated document (Year: 2019).*
(Continued)

*Primary Examiner* — Jelitza M Perez
(74) *Attorney, Agent, or Firm* — Bayramoglu Law Offices LLC

(57) ABSTRACT

An ultraviolet air sterilizer for disinfecting bacterium and virus includes a shell, a sandwich activated carbon cloth filter element, a nanometer titanium dioxide screen filter, an ultraviolet light source, a heat sinking kit, and a fan. The shell includes a shell body and a cover plate. The shell body is provided with an air inlet and an opening. The cover plate is provided with an air outlet. The sandwich activated carbon cloth filter element, the nanometer titanium dioxide screen filter, the heat sinking kit and the fan are arranged sequentially along an air path from the air inlet to the air outlet. The ultraviolet light source is configured for emitting ultraviolet light to the nanometer titanium dioxide screen filter. The air sterilizer has a compact small-sized structure and effectively removes ambient gaseous as well as particulate pollutants and kills micro-organisms harmful to health and well being.

12 Claims, 3 Drawing Sheets

(51) Int. Cl.
*B01D 53/04* (2006.01)
*B01D 53/34* (2006.01)
*B01D 53/88* (2006.01)
*H05K 7/20* (2006.01)

(56) References Cited

FOREIGN PATENT DOCUMENTS

| KR | 20150014821 A | * | 2/2015 | |
|----|---------------|---|--------|---|
| WO | WO-2019117081 A1 | * | 6/2019 | ............. A61L 9/205 |

OTHER PUBLICATIONS

Son et al. KR20150014821A—translated document (Year: 2015).*
Hidemitsu et al. WO2019117081A1—translated document (Year: 2019).*
Fujita et al. JP4448558B2—translated document (Year: 2010).*

* cited by examiner

ULTRAVIOLET AIR STERILIZER FOR DISINFECTING BACTERIUM AND VIRUS

CROSS REFERENCE TO THE RELATED APPLICATIONS

This application is based upon and claims priority to Chinese Patent Application No. 202020301887.9, filed on Mar. 12, 2020, the entire contents of which are incorporated herein by reference.

TECHNICAL FIELD

The present invention relates to air purification, and more specifically, to an ultraviolet air sterilizer for disinfecting bacterium and virus.

BACKGROUND

Air pollution sources include: (1) expired gas produced by human respiration, where oxygen is taken up by the alveoli, and then the expired gas, which contains relatively high concentrations of carbon dioxide and other undesirable gases, is discharged; (2) waste gas produced in constructions, where residential, commercial and other building construction all requires substantial material, which continuously releases waste gas and particulate matter; (3) secondhand smoke, where nicotine, tar, hydrogen cyanide and other toxic substances are produced by the combustion of tobacco, which pollutes the air as well; (4) waste gas discharged in manufacturing, and so on.

In the prior art, some air purifiers have simple structures for a single cleansing function, whereas some multifunctional purifiers have complex structures, are expensive to manufacture and take up too much space.

Therefore, a new air sterilizer is highly desirable. Such an air sterilizer should be simple, small-sized, easy-to-use and capable of purifying the ambient air disinfecting it and removing micro-organisms harmful to human health, including bacterium and virus.

SUMMARY

The purpose of the present invention is to provide a simple, small-sized and easy-to-use ultraviolet air sterilizer for effectively disinfecting bacterium and virus. The specific technical solution is as follows.

An ultraviolet air sterilizer for disinfecting bacterium and virus includes a shell, a sandwich activated carbon cloth filter element, a nanometer titanium dioxide screen filter, an ultraviolet light source, a heat sinking kit, and a fan.

The shell includes a shell body and a cover plate, wherein the shell body has a cavity. The shell body is provided with an air inlet and an opening, and the air inlet and the opening are each connected to the cavity. The cover plate is configured for opening and sealing the opening, and the cover plate is provided with an air outlet connected to the cavity. A power switch is provided on the shell body for operating the ultraviolet light source and the fan.

The sandwich activated carbon cloth filter element, the nanometer titanium dioxide screen filter, the ultraviolet light source, the heat sinking kit and the fan are each provided in the cavity of the shell body. The sandwich activated carbon cloth filter element, the nanometer titanium dioxide screen filter, the heat sinking kit and the fan are arranged sequentially along an air path from the air inlet to the air outlet, and the ultraviolet light source is configured for emitting ultraviolet light to the nanometer titanium dioxide screen filter.

Preferably in the above technical solution, the shell body has a cylindrical structure, the air inlet is provided at a lower part of a sidewall of the shell body, and the cover plate is provided at a top part of the shell body.

The sandwich activated carbon cloth filter element is located in a lower part of the cavity, and air from the air inlet flows into a middle channel of the sandwich activated carbon cloth filter element through a sidewall of the sandwich activated carbon cloth filter element.

The nanometer titanium dioxide screen filter is located directly above the sandwich activated carbon cloth filter element, so that all the gas flowing into the middle channel of the sandwich activated carbon cloth filter element passes through a nanometer titanium dioxide layer in the nanometer titanium dioxide screen filter.

The heat sinking kit is located directly above the nanometer titanium dioxide screen filter, so that the gas passing through the nanometer titanium dioxide screen filter is cooled by the heat sinking kit and then discharged from the air outlet by action of the fan.

Preferably in the above technical solution, a lower end of the heat sinking kit is provided with a quartz glass layer, and the quartz glass layer and the heat sinking kit form an integrated structure.

Preferably in the above technical solution, the sandwich activated carbon cloth filter element, the nanometer titanium dioxide screen filter, the heat sinking kit and the fan are detachably provided on an inner wall of the shell body.

Preferably in the above technical solution, a control system is further included, which is provided on the inner wall of the shell body.

The power switch includes a fan control switch for controlling the fan and an ultraviolet light source switch for controlling the ultraviolet light source, and the fan control switch and the ultraviolet light source switch are each connected to the control system.

Preferably in the above technical solution, the fan is a fan with variable-frequency drive, and the specific variable-frequency drive is that which is of the type known by skilled artisans.

Preferably in the above technical solution, the heat sinking kit includes a cylinder and heat sink fins radially arranged on an outer wall of the cylinder; a protrusion is provided on a heat sinking surface of the heat sink fin; along a height direction of the heat sink fin, a cross-section of the heat sink fin is saw-toothed, and a cross-section of the protrusion is semicircular, triangular or rectangular.

Preferably in the above technical solution, a thickness of the heat sink fin is 0.8-1.8 mm, and a height of the protrusion is 0.8-1.2 mm.

The technical solution of the present invention has the following advantages:

(1) The ultraviolet air sterilizer for disinfecting bacterium and virus of the present invention includes a shell, a sandwich activated carbon cloth filter element, a nanometer titanium dioxide screen filter, an ultraviolet light source, a heat sinking kit, and a fan, which has a compact and small structure. The sandwich activated carbon cloth filter element is configured to filter not only gaseous pollutants such as formaldehyde, but also particulate pollutants. The combination of the nanometer titanium dioxide screen filter and the ultraviolet light source can effectively reduce the odorous and harmful gases in the air and effectively kill numerous kinds of bacteria and fungi. By the combination of the sandwich activated carbon cloth filter element, the nanometer titanium dioxide screen filter, and the ultraviolet light source, in the photoreaction of the nano-photocatalyst, valence, or outer shell electrons of high energy are excited to the conduction shell to form electron holes, which have strong oxidizing properties to decompose the organic matter into carbon dioxide and water by means of destroying C—C bond, C—H bond, C—N bond, C—O bond, O—H bond, N—H bond, etc., and which kills bacteria and viruses by breaking the cell membrane of bacteria, coagulating the proteins of viruses and changing the conditions needed for growth and propagation of bacteria and viruses. The ultraviolet air sterilizer for disinfecting bacterium and virus of the present invention, therefore, has the dual function of bacteria and virus eradication.

(2) The shell body has a cylindrical structure, which is aesthetic. Moreover, the present invention arranges the sandwich activated carbon cloth filter element, the nanometer titanium dioxide screen filter, the ultraviolet light source, the heat sinking kit, and the fan in the above-mentioned manner to forms a small overall volume and is user-friendly.

(3) The lower end of the heat sinking kit in the present invention is provided with a quartz glass layer, and the quartz glass layer and the heat sinking kit form an integrated structure. The design of the quartz glass layer combined with the heat sinking kit is not only convenient for fixing the heat sinking kit, but also can well avoid the infiltration of water mist and prolong the service life of the components (4) The sandwich activated carbon cloth filter element, the nanometer titanium dioxide screen filter, the heat sinking kit, and the fan in the present invention are detachably arranged on the inner wall of the shell body, and these components can be replaced according to the use requirements, which is convenient to use and conducive to timely improving the effects of bacterium eradication and virus eradication.

(5) The present invention further includes a control system. The control system is provided on the inner wall of the shell body. The power switch includes a fan control switch for controlling the fan and an ultraviolet light source switch for controlling the ultraviolet light source. The fan control switch and the ultraviolet light source switch are each connected to the control system. The control system can control the fan and the ultraviolet light source respectively, for example, the wind speed (normal wind, natural wind, sleep wind, intelligent wind, etc.) can be changed by adjusting the voltage or current of the fan, and the light intensity and duration of the ultraviolet light source can be adjusted.

(6) The heat sinking kit in the present invention includes a cylinder and heat sink fins radially arranged on an outer wall of the cylinder. A protrusion is provided on the heat sinking surface of the heat sink fin. Along a height direction of the heat sink fin, a cross-section of the heat sink fin is saw-toothed, and a cross-section of the protrusion is semicircular, triangular or rectangular. The thickness of the heat sink fin is 0.8-1.8 mm, and the height of the protrusion is 0.8-1.2 mm. The heat sinking effect is improved by the design of the shape and size of the heat sink fin.

In addition to the purposes, features and advantages described above, the present invention has other purposes, features and advantages. The present invention will be further described in detail below with reference to the attached drawings.

BRIEF DESCRIPTION OF THE DRAWINGS

Some drawings in the present disclosure are used to provide a further understanding of the present invention, and the schematic embodiments of the present invention and their description are used to elaborate the present invention and do not constitute an undue limitation of the present invention. In the attached drawings.

Figure 1:
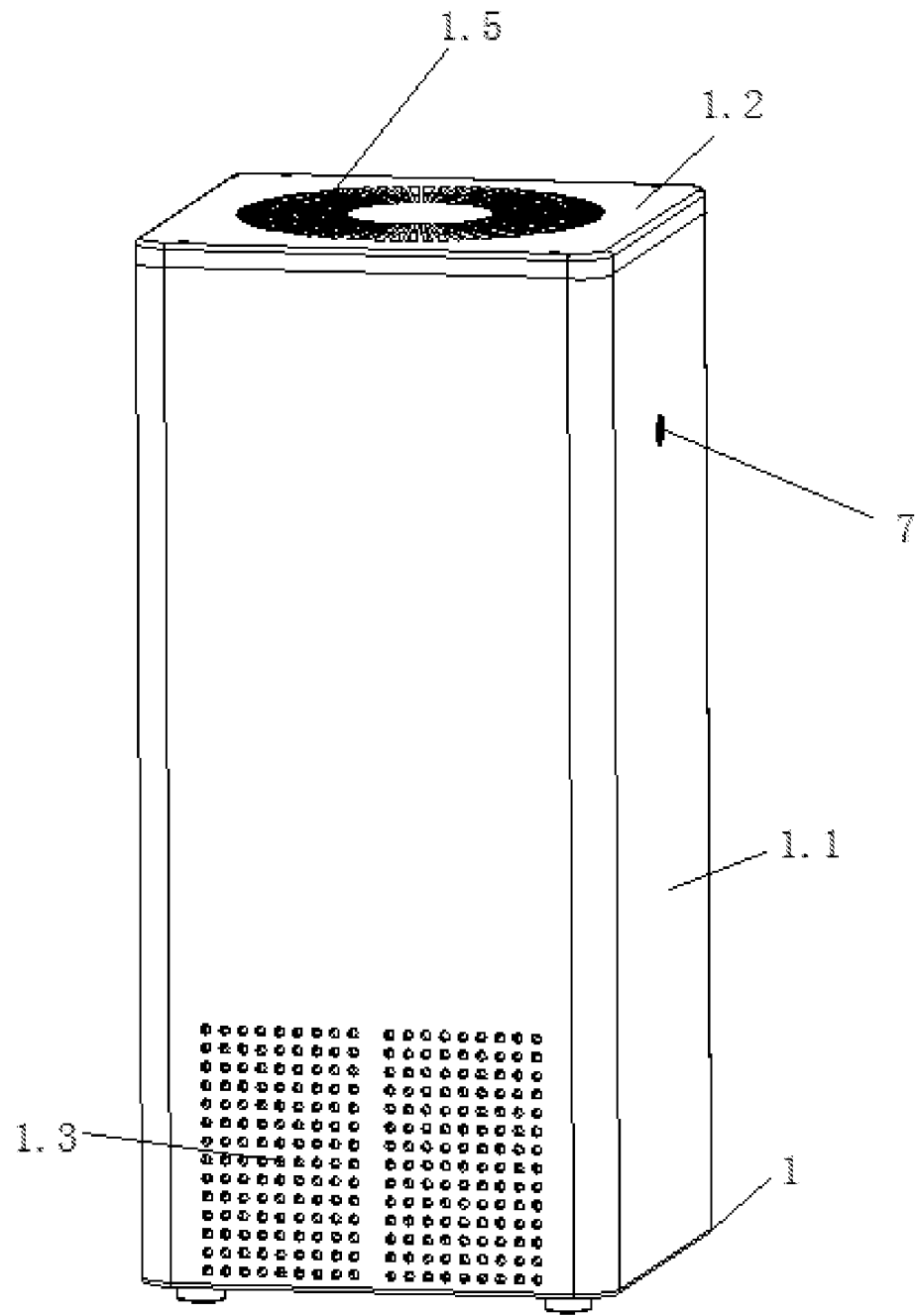
FIG. 1 is a schematic diagram of an overall structure of an ultraviolet air sterilizer for disinfecting bacterium and virus in an embodiment.

In the drawings, 1—shell, 1.1—shell body, 1.2—cover plate, 1.3—air inlet, 1.4—opening, 1.5—air outlet, 1.6—baffle, 2—sandwich activated carbon cloth filter element, 3—nanometer titanium dioxide screen filter, 4—ultraviolet light source, 5—heat sinking kit, 5.1—fixing frame, 6—fan, 7—power switch, 8—control system, and 9—quartz glass layer, 10—heat sink fin, 10.1—protrusion.

DETAILED DESCRIPTION OF THE EMBODIMENTS

One embodiment of the present invention is described in detail with reference to the attached drawings, but the present invention can be implemented in a variety of different embodiments according to the limitation and scope of the claims.

Embodiment

Figure 2:
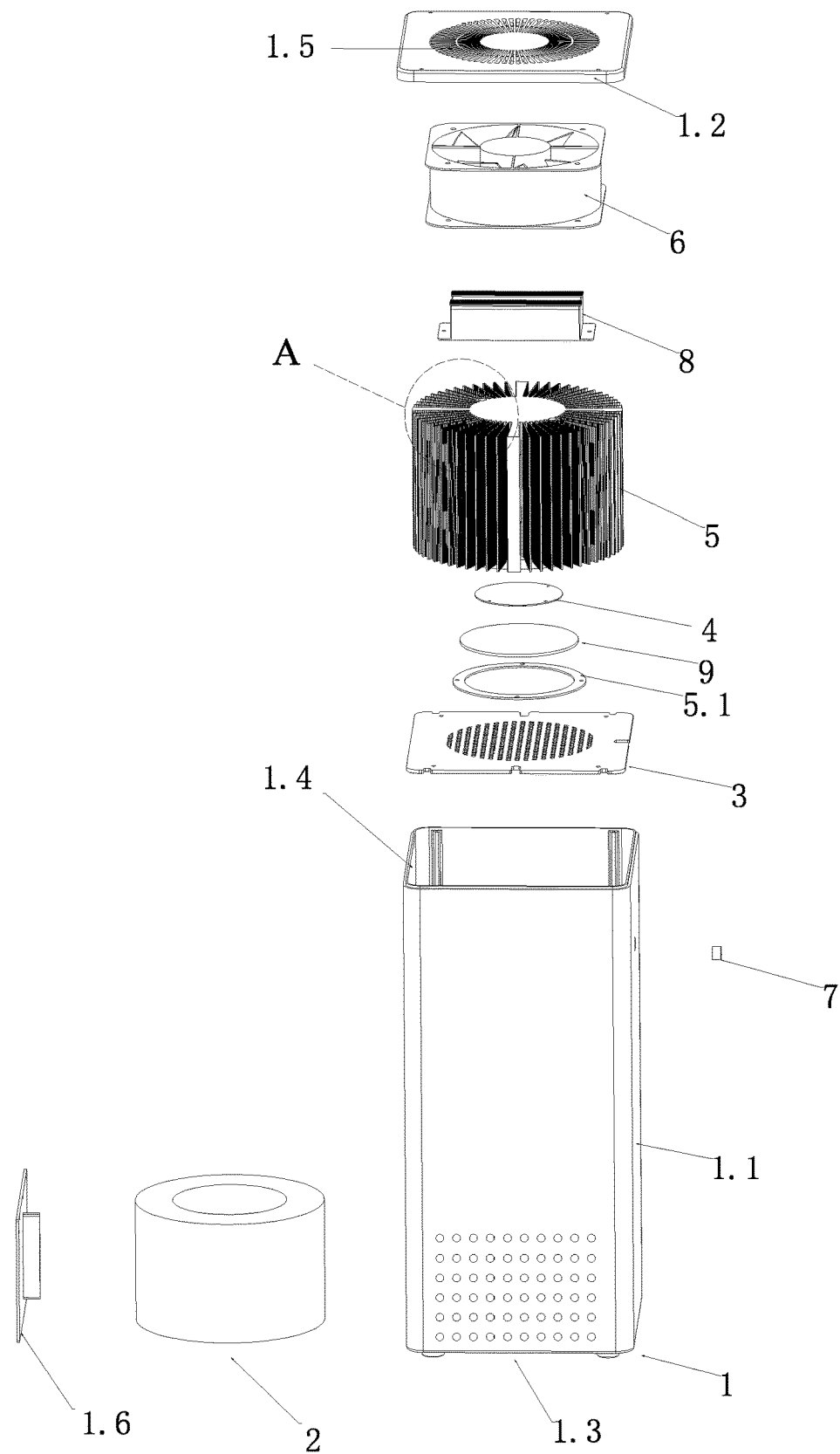
FIG. 2 is an exploded view showing the structure in FIG. 1.

An ultraviolet air sterilizer for disinfecting bacterium and virus, referring to FIGS. 1-2, includes the shell 1, the sandwich activated carbon cloth filter element 2, the nanometer titanium dioxide screen filter 3, the ultraviolet light source 4, the heat sinking kit 5 and the fan 6. The details are as follows:

The shell 1 includes the shell body 1.1 and the cover plate 1.2. The shell body 1.1 has a cylindrical structure with a cavity and the opening 1.4 composed of a bottom part, a sidewall and a rear cover, referring to FIGS. 1-2. The lower part of the rear cover is provided with the air inlet 1.3 connected to the cavity, and the opening 1.4 is provided at the top part of the shell body 1.1. The cover plate 1.2 is configured for opening and sealing the opening 1.4, and is provided with the air outlet 1.5 connected to the cavity. The sidewall of the shell body 1.1 is provided with the power switch 7 for turning on the ultraviolet light source 4 and the fan 6, wherein the power switch includes a fan control switch for controlling the fan and an ultraviolet light source switch for controlling the ultraviolet light source. The fan 6 is preferably a fan with the variable-frequency drive. The outside of each of the air inlet 1.3 and the air outlet 1.5 may further be provided with the baffle 1.6 configured to seal the air inlet and air outlet and keep the air inlet and air outlet clean.

The sandwich activated carbon cloth filter element 2, the nanometer titanium dioxide screen filter 3, the ultraviolet light source 4, the heat sinking kit 5, and the fan 6 are all provided in the cavity of the shell body 1.1. The sandwich activated carbon cloth filter element 2, the nanometer titanium dioxide screen filter 3, the heat sinking kit 5 and the fan 6 are arranged sequentially along the air path from the air inlet 1.3 to the air outlet 1.5. Specifically, the sandwich activated carbon cloth filter element 2 is located in a lower part of the cavity, and air from the air inlet 1.3 flows into a middle channel of the sandwich activated carbon cloth filter element 2 through the sidewall of the sandwich activated carbon cloth filter element 2. The nanometer titanium dioxide screen filter 3 is located directly above the sandwich activated carbon cloth filter element 2, causing all the gas flowing into the middle channel of the sandwich activated carbon cloth filter element to pass through a nanometer titanium dioxide layer in the nanometer titanium dioxide screen filter 3. The heat sinking kit 5 is located directly above the nanometer titanium dioxide screen filter 3, causing the gas passing through the nanometer titanium dioxide screen filter 3 to be cooled by the heat sinking kit and then to be discharged from the air outlet 1.5 by an action of the fan 6. The ultraviolet light source 4 is fixed on the sidewall of the shell body 1.1 and is configured for emitting ultraviolet light to the nanometer titanium dioxide screen filter 3, so that under the ultraviolet light, the electrons in the valence band of the nanometer carbon dioxide catalyst layer in the nanometer titanium dioxide screen filter 3 are excited to the conduction band under the light irradiation of a nanophotocatalyst to form electrons and holes, which has a strong oxidizing property to decompose the organic matter into carbon dioxide and water by means of destroying C—C bond, C—H bond, C—N bond, C—O bond, O—H bond, N—H bond, etc., and which meanwhile kills the bacteria and viruses by breaking the cell membrane of bacteria, coagulating the proteins of viruses, and changing the living surroundings of the bacteria and viruses.

Figure 3:
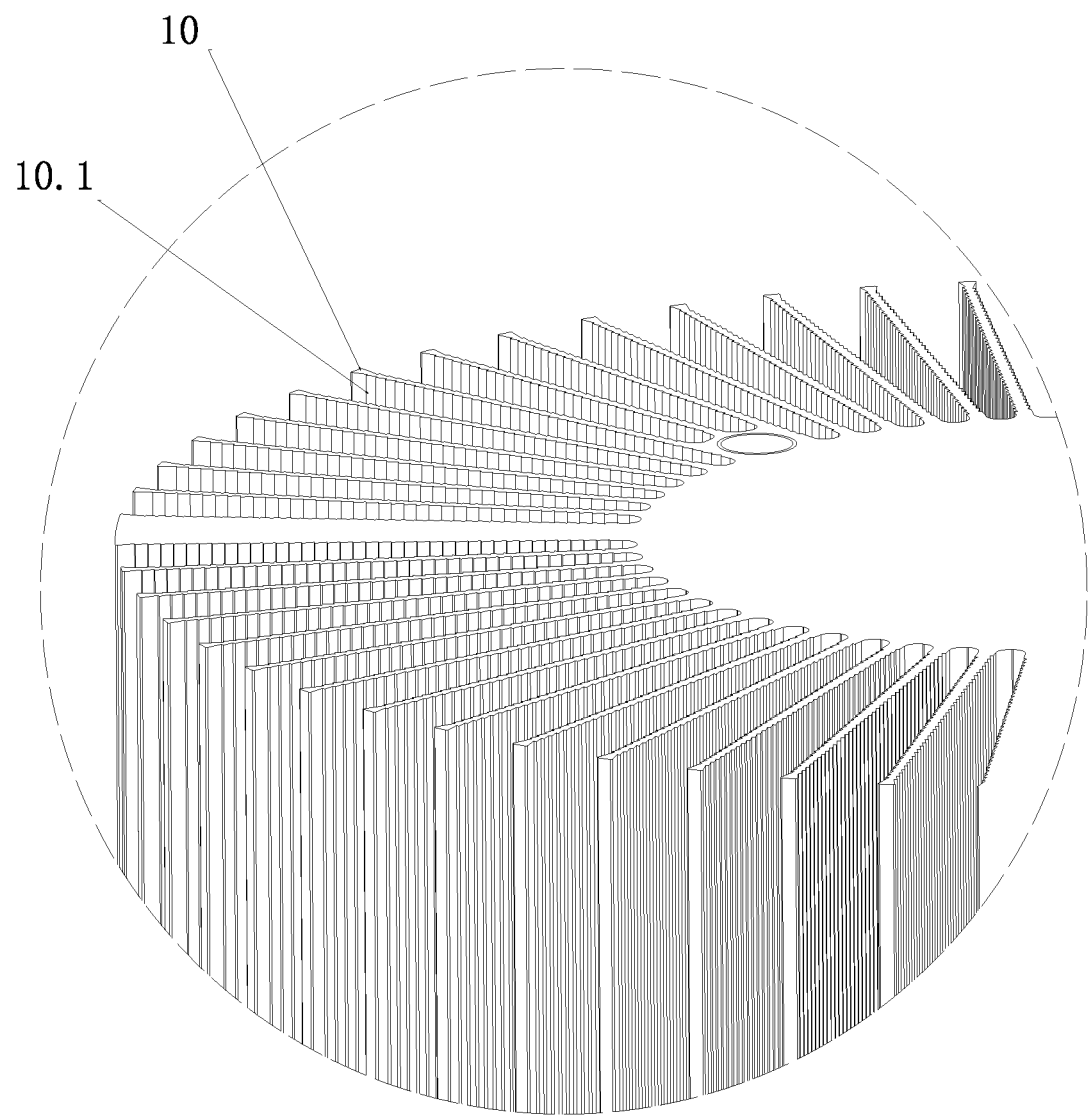
FIG. 3 is an enlarged view showing the portion A in FIG. 2.

In this embodiment, the lower end of the heat sinking kit 5 is provided with the quartz glass layer 9. The quartz glass layer 9 and the heat sinking kit 5 form an integrated structure. Specifically, the quartz glass layer 9 is fixed on the surface of the lower end of the heat sinking kit 5 by the fixing frame 5.1. The heat sinking kit 5 includes a cylinder and heat sink fins 10 radially arranged on the outer wall of the cylinder. As shown in FIG. 3, the protrusion 10.1 is provided on a heat sinking surface of the heat sink fin 10. Along a height direction of the heat sink fin 10, a cross-section of the heat sink fin 10 is saw-toothed, and a cross-section of the protrusion 10.1 is semicircular, triangular or rectangular. The thickness of the heat sink fin 10 is 0.8-1.8 mm, and the height of the protrusion 10.1 is 0.8-1.2 mm. Preferably, the quartz glass layer and the cylinder in the heat sinking kit are arranged coaxially, and the diameter of the quartz glass layer is 0.2-0.6 times the diameter of the cylinder.

In this embodiment, the sandwich activated carbon cloth filter element 2, the nanometer titanium dioxide screen filter 3, the heat sinking kit 5, and the fan 6 are detachably provided on the inner surface of the sidewall of the shell body 1.1 by bolts or screws. The sandwich activated carbon cloth filter element and the nanometer titanium dioxide screen filter can be replaced after opening the rear cover. The heat sinking kit and the fan can be replaced after opening the cover plate 1.2.

In addition, the embodiment may further include the control system 8, which is arranged on the inner wall of the shell body 1.1, and the fan control switch and the ultraviolet light source switch are each connected to the control system 8. The control system herein includes a control chip, or other components that can realize intelligent control with reference to prior arts.

In addition, this embodiment may further provided with a WiFi module, a smart quick-connect module, a remote control module for a mobile phone, a particle laser sensor, a temperature and humidity sensor, a wind speed adjustment module, an air quality detection module, a filter element replacement reminder module, and other functional modules, where the intelligent module can be customized according to user needs.

In addition, the lower end of the shell 1 may further be provided with a rolling wheel group (including at least one roller) to facilitate the movement.

The ultraviolet air sterilizer for disinfecting bacterium and virus of this embodiment has the following effects. (1) The ultraviolet air sterilizer for disinfecting bacterium and virus can destroy the C—C bond, C—H bond, C—N bond, C—O bond, O—H bond, and N—H bond in organic matters, and decompose the organic matters into carbon dioxide and water.

Meanwhile, the ultraviolet air sterilizer for disinfecting bacterium and virus can destroy the cell membrane of bacteria, coagulate the proteins of viruses, and change the conditions requisite for the growth and propagation of bacteria and viruses, thereby eradicating the bacteria and viruses. The ultraviolet air sterilizer for disinfecting bacterium and virus employs a physical sterilization method, which is safe and non-toxic, without ozone and secondary pollutants produced. (2) The ultraviolet air sterilizer for disinfecting bacterium and virus can purify formaldehyde, benzene, ammonia, sulfur dioxide, carbon monoxide, nitrogen oxides and other harmful organic compounds that affect human health, and also can deodorize cigarette odor, toilet odor, garbage odor, animal odor, etc. (3) The sandwich activated carbon cloth filter element, the nanometer titanium dioxide screen filter and the ultraviolet light source are combined to realize the energy-saving purpose. (4) The ultraviolet air sterilizer for disinfecting bacterium and virus is suitable for individuals, families, organizations and other public places.

The above are only the preferred embodiments of the present invention and are not intended to limit the present invention. Those skilled in the art can make various modifications and amendments to the present invention. Any modification, equivalent replacement, improvement, etc. made within the spirit and principles of the present invention shall fall within the protection scope of the present invention.

What is claimed is:

1. An ultraviolet air sterilizer for disinfecting bacterium and virus, comprising a shell, a sandwich activated carbon cloth filter element, a nanometer titanium dioxide screen filter, an ultraviolet light source, a heat sinking kit, a fan and a control system; wherein the shell comprises a shell body and a cover plate, wherein the shell body has a cavity; the shell body is provided with an air inlet and an opening; the air inlet and the opening are each connected to the cavity; the cover plate is configured for opening and sealing the opening; the cover plate is provided with an air outlet connected to the cavity; a power switch for turning on the ultraviolet light source and the fan is provided on the shell body;

the sandwich activated carbon cloth filter element, the nanometer titanium dioxide screen filter, the ultraviolet light source, the heat sinking kit and the fan are provided in the cavity of the shell body; the sandwich activated carbon cloth filter element, the nanometer titanium dioxide screen filter, the heat sinking kit and the fan are arranged sequentially along an air path from the air inlet to the air outlet; and the ultraviolet light source is configured for emitting ultraviolet light to the nanometer titanium dioxide screen filter, the control system is provided on an inner wall of the shell body, and the power switch comprises a fan control switch for controlling the fan and an ultraviolet light source switch for controlling the ultraviolet light source, and each of the fan control switch and the ultraviolet light source switch is connected to the control system; and the heat sinking kit comprises a cylinder and heat sink fins radially arranged on an outer wall of the cylinder; a protrusion is provided on a heat sinking surface of each of the heat sink fins; along a height direction of each of the heat sink fins, a cross-section of each of the heat sink fins is saw-toothed, and a cross-section of the protrusion is semicircular, triangular or rectangular.

2. The ultraviolet air sterilizer according to claim 1, wherein the shell body has a cylindrical structure, the air inlet is provided at a lower part of a sidewall of the shell body, and the cover plate is provided at a top part of the shell body;

the sandwich activated carbon cloth filter element is located in a lower part of the cavity, and air from the air inlet flows into a middle channel of the sandwich activated carbon cloth filter element through a sidewall of the sandwich activated carbon cloth filter element;

the nanometer titanium dioxide screen filter is located directly above the sandwich activated carbon cloth filter element, and the air flowing into the middle channel of the sandwich activated carbon cloth filter element passes through a nanometer titanium dioxide layer in the nanometer titanium dioxide screen filter; and the heat sinking kit is located directly above the nanometer titanium dioxide screen filter, and the air passing through the nanometer titanium dioxide screen filter is cooled by the heat sinking kit and then the air is discharged from the air outlet by the fan.

3. The ultraviolet air sterilizer according to claim 2, wherein a lower end of the heat sinking kit is provided with a quartz glass layer, and the quartz glass layer and the heat sinking kit form an integrated structure.

4. The ultraviolet air sterilizer according to claim 2, wherein the sandwich activated carbon cloth filter element, the nanometer titanium dioxide screen filter, the heat sinking kit and the fan are detachably provided on an inner wall of the shell body.

5. The ultraviolet air sterilizer according to claim 1, wherein the fan has a variable-frequency drive.

6. The ultraviolet air sterilizer according to claim 1, wherein a thickness of each of the heat sink fins is 0.8-1.8 mm, and a height of the protrusion is 0.8-1.2 mm.

7. The ultraviolet air sterilizer according to claim 2, wherein the fan has a variable-frequency drive.

8. The ultraviolet air sterilizer according to claim 3, wherein the fan has a variable-frequency drive.

9. The ultraviolet air sterilizer according to claim 4, wherein the fan has a variable-frequency drive.

10. The ultraviolet air sterilizer according to claim 2, wherein a thickness of each of the heat sink fins is 0.8-1.8 mm, and a height of the protrusion is 0.8-1.2 mm.

11. The ultraviolet air sterilizer according to claim 3, wherein a thickness of each of the heat sink fins is 0.8-1.8 mm, and a height of the protrusion is 0.8-1.2 mm.

12. The ultraviolet air sterilizer according to claim 4, wherein a thickness of each of the heat sink fins is 0.8-1.8 mm, and a height of the protrusion is 0.8-1.2 mm.

* * * * *